US009851358B2

(12) United States Patent
Legembre et al.

(10) Patent No.: US 9,851,358 B2
(45) Date of Patent: Dec. 26, 2017

(54) METHODS AND PHARMACEUTICAL COMPOSITIONS FOR PREVENTING OR REDUCING METASTATIC DISSEMINATION

(71) Applicants: INSERM (Institut National de la Sante et de la Recherche Medicale, Paris (FR); Universite Paul Sabatier Toulouse III, Toulouse (FR); Centre Hospitalier Universitaire de Toulouse, Toulouse (FR); Universite de Bourgogne, Dijon (FR); Universite de Rennes 1, Rennes (FR); Universite des Antilles et de la Guyane, Pointe-a-Pitre (FR); Ecole des Hautes Etudes en Sante Publique (EHESP), Rennes (FR)

(72) Inventors: Patrick Legembre, Rennes (FR); Bruno Segui, Toulouse (FR); Thierry Levade, Toulouse (FR); Olivier Micheau, Dijon (FR)

(73) Assignees: INSERM (Institut National de la Sante et de la Recherche Medicale), Paris (FR); Universite Paul Sabatier Toulouse III, Toulouse (FR); Centre Hospitalier Universitaire de Toulouse, Toulouse (FR); Universite de Bourgogne, Dijon (FR); Universite de Rennes I, Rennes (FR); Universit des Antilles et de la Guiyane, Pointe-a-pitre (FR); Ecole des Hautes Etudes en Sante Publique (EHESP), Rennes (FR)

( * ) Notice: Subject to any disclaimer, the term of this patent is extended or adjusted under 35 U.S.C. 154(b) by 0 days.

(21) Appl. No.: 15/109,942

(22) PCT Filed: Jan. 7, 2015

(86) PCT No.: PCT/EP2015/050154
§ 371 (c)(1),
(2) Date: Jul. 6, 2016

(87) PCT Pub. No.: WO2015/104284
PCT Pub. Date: Jul. 16, 2015

(65) Prior Publication Data
US 2016/0327561 A1 Nov. 10, 2016

(30) Foreign Application Priority Data
Jan. 8, 2014 (EP) ..................................... 14305019

(51) Int. Cl.
*G01N 33/574* (2006.01)
*A61K 31/164* (2006.01)
*A61K 9/127* (2006.01)

(52) U.S. Cl.
CPC ....... *G01N 33/57484* (2013.01); *A61K 9/127* (2013.01); *A61K 31/164* (2013.01); *G01N 33/57415* (2013.01); *G01N 2800/52* (2013.01)

(58) Field of Classification Search
None
See application file for complete search history.

(56) References Cited

U.S. PATENT DOCUMENTS

2008/0045470 A1* 2/2008 Bielawska ............ C07C 215/18
514/44 R

FOREIGN PATENT DOCUMENTS

| JP | 10 310596 A | 11/1998 |
|---|---|---|
| WO | 99/41266 A1 | 8/1999 |
| WO | 00/59517 A | 10/2000 |

OTHER PUBLICATIONS

Schiffmann et al (Carcinogenesis, 2009, 30:745-752).*
Tran et al (Clinical Cancer Research, 2008, 14:3571-3581).*
Voelkel-Johnson et al.; "Resistance to TRAIL is associated with defects in ceramide signaling that can be overcome by exogenous C6-ceramide without requiring down-regulation of cellular FLICE inhibitory protein"; Molecular Cancer Therapeutics, vol. 4, No. 9, Sep. 1, 2005, pp. 1320-1327.
Koshkaryev et al; "Increased apoptosis in cancer cells in vitro and in vivo by ceramides in transferrin-modified liposomes"; Cancer Biology & Therapy, vol. 13, No. 1, Jan. 1, 2012, pp. 50-60.
Ozawa et al.; "Sulfatides Inhibit Adhesion, Migration, and Invasion of Murine Melanoma B16F10 Cell Line in Vitro"; Biological & Pharmaceutical Bulletin, vol. 35, No. 11, Jan. 1, 2012, pp. 2054-2058.
Hu et al.; "Prosaposin down-modulation decreases metastatic prostate cancer cell adhesion, migration, and invasion"; Molecular Cancer 2010, vol. 9, 2010, pp. 1-18.
(Continued)

*Primary Examiner* — Laura B Goddard
(74) *Attorney, Agent, or Firm* — Whitham Curtis & Cook, PC

(57) ABSTRACT

The present invention relates to methods and pharmaceutical compositions for preventing or reducing metastatic dissemination (i.e. reducing motility of cancer cells). In particular, the present invention relates to a method for preventing or reducing metastatic dissemination (i.e. reducing motility of cancer cells) in a subject suffering from a cancer comprising the steps consisting of i) determining the expression level of at least one biomarker selected from the group consisting of soluble CD95L and EMT promoting factors in a sample obtained from the subject, ii) comparing the expression level determined at step i) with a predetermined reference value and iii) administering the subject with a therapeutically effective amount of C16-ceramide or derivatives such as C16-sphingomyelin and C16-glycosphingolipids when the expression level determined at step i) is higher than the predetermined reference value.

5 Claims, 2 Drawing Sheets

(56) References Cited

OTHER PUBLICATIONS

Figure 1A:
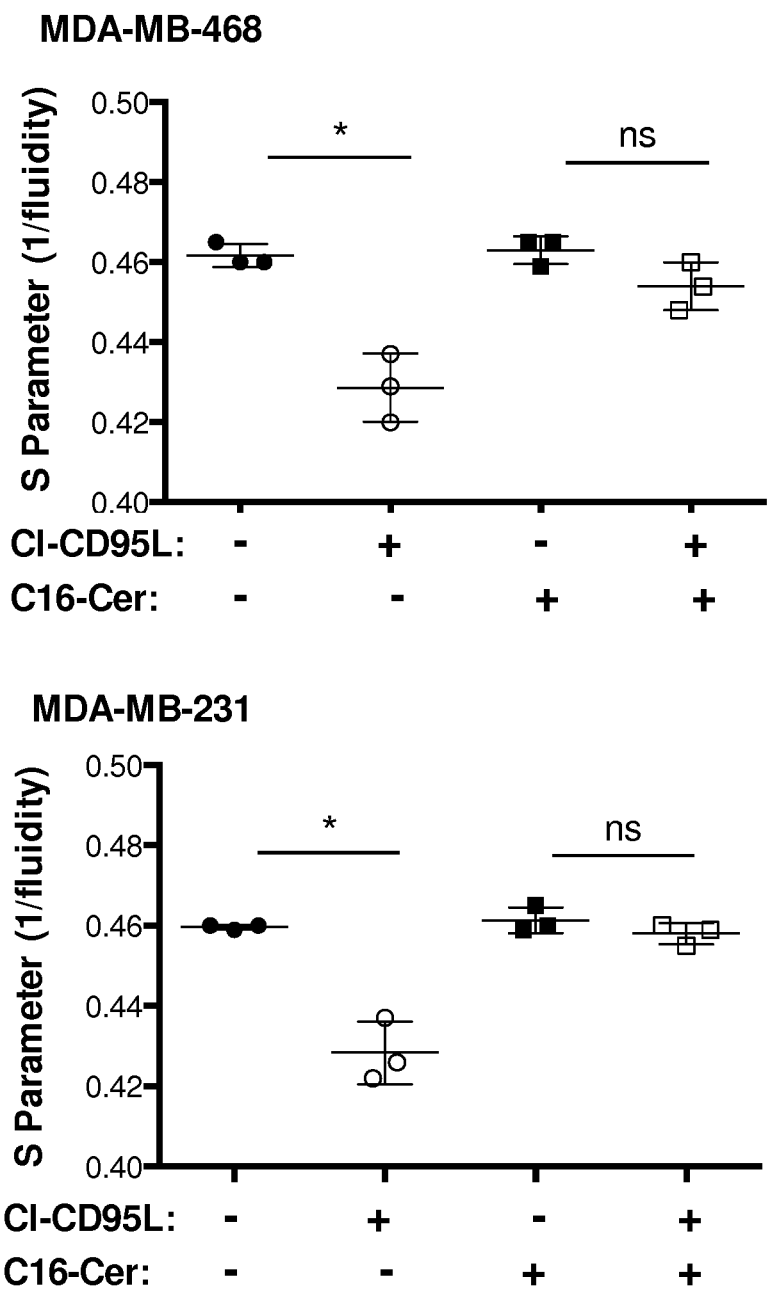

Edmond et al.; "Downregulation of ceramide synthase-6 during epithelial-to-mesenchymal transition reduces plasma membrane fluidity and cancer cell motility"; Oncogene, Mar. 17, 2014, pp. 1-10.
Bieberich et al.; "Synthesis and characterization of novel ceramide analogs for induction of apoptosis in human aancer cells"; Cancer Letters, vol. 181, No. 1, Jul. 8, 2002, pp. 55-64.
Shabbits et al.; "Intracellular delivery of ceramide lipids via liposomes enhances apoptosis in vitro"; Biochimica et Biophysica Acta (BBA), vol. 1612, No. 1, May 2, 2003, pp. 98-106.

\* cited by examiner

METHODS AND PHARMACEUTICAL COMPOSITIONS FOR PREVENTING OR REDUCING METASTATIC DISSEMINATION

FIELD OF THE INVENTION

The present invention relates to methods and pharmaceutical compositions for preventing or reducing metastatic dissemination (i.e. reducing motility of cancer cells).

BACKGROUND OF THE INVENTION

CD95L (also known as FasL) is a transmembrane ligand that binds to the so-called death receptor CD95 (also known as Fas/APO1). Metalloproteases can cleave CD95L to produce the soluble ligand cl-CD95L. While transmembrane CD95L is a potent apoptosis inducer that participates in immune surveillance and tolerance (see review[32]), cl-CD95L cannot induce apoptosis, but instead triggers the motility of cancer cells and activated T lymphocytes[12, 15, 34] and aggravates inflammation[23, 34]. Binding of transmembrane CD95L to CD95 leads to formation of the death-inducing signaling complex (DISC), which contains the Fas-associated death domain adaptor protein and caspases -8 and -10[14]. This complex plays a pivotal role in the initiation of apoptotic signaling. Cells can be classified as type I or type II according to the efficiency with which DISC forms and their reliance on the mitochondrion-driven apoptotic signal to implement the CD95-mediated apoptotic signal[14]. It was previously shown that type II cells are of epithelial lineage, whereas type I cells are mesenchymal-like[1]. Type II cells are more sensitive to the CD95-mediated apoptotic signal than type I cells; therefore, it was concluded that cancer cells undergoing epithelial-to-mesenchymal transition (EMT) reprogram their apoptotic machinery to resist CD95-mediated cell death 1. These findings encouraged the inventors to investigate whether EMT alters the cellular response to cl-CD95L, i.e., motility.

Sphingolipids (SLs) belong to a class of lipids whose members play multiple roles in eukaryotic cells. SLs are important structural components of membranes and are second messengers that regulate cell growth, differentiation, and death[10]. Ceramide (N-acyl-D-erythro-sphingosine) can be generated via hydrolysis of sphingomyelin by sphingomyelinases, or via ceramide synthase (CerS)-mediated de novo ceramide biosynthesis. This pathway involves acylation of sphinganine with fatty acyl-CoAs of chain lengths of C14-C26 to produce dihydroceramide. Alternatively, CerS can synthesize ceramide by the salvage pathway through direct acylation of sphingosine, which is derived from SL catabolism[10]. Ceramide synthesis is orchestrated by six mammalian CerS proteins, each of which produces ceramides with restricted acyl chain lengths[20]. Among these proteins, ceramide synthase isoform 6 (CerS6) was most recently cloned[37]. Although most studies on ceramides have analyzed their impact on apoptotic signaling, these lipids also promote the formation of ordered liquid phases called lipid rafts, whose accumulation rigidifies the plasma membrane[28]. Ceramides form rigid ceramide-enriched domains when their N-acyl chain is longer than C12[5, 7] and lead to an overall decrease in ordered lipid membranes in CerS2-null mice[29]. The biophysical properties of hepatocyte membranes are modified in CerS2-null mice, including increased fluidity[24], which is directly associated with changes in the SL composition. Furthermore, high plasma membrane fluidity is correlated with enhanced migratory/invasive ability of tumor cells[22, 30, 33, 39], which might be due to the enhanced deformability of these cells[22]. These observations raise the possibility that EMT alters the level of SL biosynthesis to increase membrane fluidity, which in turn promotes cell migration, a phenotypic change associated with EMT.

SUMMARY OF THE INVENTION

The present invention relates to methods and pharmaceutical compositions for preventing or reducing metastatic dissemination (i.e. reducing motility of cancer cells).

DETAILED DESCRIPTION OF THE INVENTION

Electron paramagnetic resonance was used to show that EMT and cl-CD95L treatment both led to augmentation of plasma membrane fluidity that was instrumental in inducing cell migration. Compaction of the plasma membrane is modulated, among other factors, by the ratio of certain lipids such as sphingolipids in the membrane. An integrative analysis of gene expression in NCI tumor cell lines revealed that expression of ceramide synthase-6 (CerS6) decreased during EMT. Furthermore, pharmacological and genetic approaches established that modulation of CerS6 expression/activity in cancer cells altered the level of C16-ceramide, which in turn influenced plasma membrane fluidity and cell motility. Therefore, the inventors identify CerS6 as a novel EMT-regulated gene that plays a pivotal role in the regulation of cell migration.

Thus an aspect of the invention relates to a method for preventing or reducing metastatic dissemination (i.e. reducing motility of cancer cells) in a subject suffering from a cancer comprising the steps consisting of i) determining the expression level of at least one biomarker selected from the group consisting of soluble CD95L and EMT promoting factors in a sample obtained from the subject, ii) comparing the expression level determined at step i) with a predetermined reference value and iii) administering the subject with a therapeutically effective amount of at least one compound selected from the group consisting of C16-ceramide, C16-sphingomyelin and C16-glycosphingolipid when the expression level determined at step i) is higher than the predetermined reference value.

In some embodiments, the subject suffers from a cancer selected from the group consisting of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. Thus, the method for the present invention is generally applicable to any type of cancer in which EMT occurs. In certain embodiments, the cancer is a solid tumor malignancy. In certain embodiments, the cancer is breast, colon, or prostate cancer. In a particular embodiment, cancer is a triple negative breast cancer. As used herein the expression "Triple negative breast cancer" has its general meaning in the art and means that said breast cancer lacks receptors for the hormones estrogen (ER-negative) and progesterone (PR-negative), and for the protein HER2.

In some embodiments, the sample is a blood sample. By "blood sample" is meant a volume of whole blood or fraction thereof, eg, serum, plasma, etc.

As used herein, the term "EMT-promoting factor" refers to any factor, typically a protein that is able to promote epithelial-to-mesenchymal transition. In a particular embodiment, the EMT-promoting factor is TGFbeta. "TGF-beta", as used herein means TGFbeta-1, TGFbeta-2, or TGFbeta-3 (Schmierer, B. and Hill, C. (2007) Nat Rev Mol Cell Biol. 8(12): 970-82), or heterodimers thereof. Additional EMT-promoting factors include but are not limited to the proteins HGF (Lamorte, L. et al (2002) Mol Biol Cell. 13(5): p. 1449-61), Hedgehog (Feldmann, G. et al (2007) Cancer Res. 67(5): p. 2187-96), Wnt (Yook, J. et al (2006) Nat Cell Biol. 8(12): p. 1398-406), IL-1 (Chaudhuri, V. et al (2007) J Cutan Pathol. 34(2): p. 146-53), Oncostatin M (Pollack, V. et al (2007) Am J Physiol Renal Physiol. 293(5): p. F1714-26), EGF (Solic, N. and Davies, D. (1997) Exp Cell Res. 234(2): p. 465-76), Amphiregulin (Chung, (2005) E. Exp Cell Res. 309(1): p. 149-60), HB-EGF (Wang, F. et al (2007) Cancer Res. 67(18): p. 8486-93), MSP (Camp, E., (2007) Cancer. 109(6): p. 1030-9), Wnt5a (Dissanayake, S. (2007) J Biol Chem. 282(23): p. 17259-71; Ripka, S. (2007) Carcinogenesis. 28(6): p. 1178-87), and TNF-alpha (Bates, R. and Mercurio, A. (2003) Mol Biol Cell. 14(5): p. 1790-800). Alternatively, the tumor cells may be engineered to inducibly-express a protein that causes the cells to undergo EMT, e.g. Snail, Zeb1 or TGF-beta As used herein, the term "CD95" has its general meaning in the art and refers to CD95 to the receptor present on the surface of mammalian cells, which has been originally shown to have the capacity to induce apoptosis upon binding of the trimeric form of its cognate ligand, CD95L (Krammer, P. H. (2000). CD95's deadly mission in the immune system. Nature 407, 789-795). CD95 is also known as Fas or Apo-1. As used herein the term CD95L has its general meaning in the art and refers to the cognate ligand of CD95 that is a transmembrane protein.

As used herein the term "soluble CD95L" has its general meaning in the art and refers to the soluble ligand produced by the cleavage of the transmembrane CD95L (also known as FasL) (Matsuno et al., 2001; Vargo-Gogola et al., 2002; Kiaei et al., 2007; Kirkin et al., 2007; or Schulte et al., 2007). The term "serum CD95L", "soluble CD95L", "metalloprotease-cleaved CD95L" and "cl-CD95L" have the same meaning along the specification.

A predetermined reference value can be relative to a number or value derived from population studies, including without limitation, subjects of the same or similar age range, subjects in the same or similar ethnic group, and subjects having the same severity of cancer. Such predetermined reference values can be derived from statistical analyses and/or risk prediction data of populations obtained from mathematical algorithms and computed indices of metastatic dissemination. In one embodiment of the present invention, the predetermined reference values are derived from the level of selected biomarker of the invention (e.g. soluble CD95L) in a control sample derived from one or more subjects who were not subjected to metastatic dissemination. Furthermore, retrospective measurement of the level of the selected biomarker (e.g. soluble CD95L) in properly banked historical subject samples may be used in establishing these predetermined reference values. Typically, the levels of the selected biomarker (e.g. soluble CD95L) in a subject having metastatic dissemination is deemed to be higher than the reference value obtained in a subject for whom metastatic dissemination did not occur.

In some embodiments, the predetermined reference value is correlated with the risk of relapse and distant metastasis, the duration of the disease-free survival (DFS) and/or the overall survival (OS). Accordingly, the predetermined reference value may be typically determined by carrying out a method comprising the steps of a) providing a collection of blood samples from subject suffering from the same cancer;

b) providing, for each blood sample provided at step a), information relating to the actual clinical outcome for the corresponding subject (i.e. risk of relapse and distant metastasis, the duration of the disease-free survival (DFS) and/or the overall survival (OS));

c) providing a serial of arbitrary quantification values;

d) determining the level of the selected biomarker (e.g. soluble CD95L) for each blood sample contained in the collection provided at step a);

e) classifying said blood samples in two groups for one specific arbitrary quantification value provided at step c), respectively: (i) a first group comprising blood samples that exhibit a quantification value for level that is lower than the said arbitrary quantification value contained in the said serial of quantification values; (ii) a second group comprising blood samples that exhibit a quantification value for said level that is higher than the said arbitrary quantification value contained in the said serial of quantification values; whereby two groups of blood samples are obtained for the said specific quantification value, wherein the blood samples of each group are separately enumerated;

f) calculating the statistical significance between (i) the quantification value obtained at step e) and (ii) the actual clinical outcome of the patients from which blood samples contained in the first and second groups defined at step f) derive;

g) reiterating steps f) and g) until every arbitrary quantification value provided at step d) is tested;

h) setting the said predetermined reference value as consisting of the arbitrary quantification value for which the highest statistical significance (most significant) has been calculated at step g).

For example the expression level of the selected biomarker (e.g. soluble CD95L) has been assessed for 100 blood samples of 100 patients. The 100 samples are ranked according to the expression level of the selected biomarker (e.g. soluble CD95L). Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the expression level of the selected biomarker (e.g. soluble CD95L) corresponding to the boundary between both subsets for which the p value is minimum is considered as the predetermined reference value. It should be noted that the predetermined reference value is not necessarily the median value of levels of the selected biomarker (e.g. soluble CD95L).

Thus in some embodiments, the predetermined reference value thus allows discrimination between an increased risk of relapse and distant metastasis and a decreased risk of relapse and distant metastasis (or a poor and a good prognosis with respect to DFS and OS for a patient). Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above.

For example, according to this specific embodiment of a "cut-off" value, the outcome can be determined by comparing the expression level of the selected biomarker (e.g. soluble CD95L) with the range of values which are identified. In certain embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. Therefore, a patient may be assessed by comparing values obtained by measuring the expression level of the selected biomarker (e.g. soluble CD95L), where values greater than 5 reveal an increased risk of relapse and distant metastasis (or a poor prognosis) and values less than 5 reveal a decreased risk of relapse and distant metastasis (or a good prognosis). In a another embodiment, a patient may be assessed by comparing values obtained by measuring the expression level of the selected biomarker (e.g. soluble CD95L) and comparing the values on a scale, where values above the range of 4-6 indicate an increased risk of relapse and distant metastasis (or a poor prognosis) and values below the range of 4-6 indicate a decreased risk of relapse and distant metastasis (or a good prognosis), with values falling within the range of 4-6 indicating an intermediate occurrence (or prognosis).

Typically, when the subject suffers from triple negative breast cancer the predetermined reference value may be 80 pg/ml or 120 pg/ml for soluble CD95L (Malleter M, Tauzin S, Bessede A, Castellano R, Goubard A, Godey F, Levêque J, Jézéquel P, Campion L, Campone M, Ducret T, Macgrogan G, Debure L, Collette Y, Vacher P, Legembre P. CD95L cell surface cleavage triggers a prometastatic signaling pathway in triple-negative breast cancer. Cancer Res. 2013 Nov. 15; 73(22):6711-21.).

According to the invention, the measure of the expression level of the selected biomarker (e.g. soluble CD95L) can be performed by a variety of techniques. Typically, the methods may comprise contacting the sample with a binding partner capable of selectively interacting with soluble CD95L in the sample. In some aspects, the binding partners are antibodies, such as, for example, monoclonal antibodies or even aptamers.

The aforementioned assays generally involve the binding of the partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The expression level of the selected biomarker (e.g. soluble CD95L) may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

An exemplary biochemical test for identifying specific proteins employs a standardized test format, such as ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available. Therefore ELISA method can be used, wherein the wells of a microtiter plate are coated with a set of antibodies which recognize the selected biomarker (e.g. soluble CD95L). A sample containing or suspected of containing the selected biomarker (e.g. soluble CD95L) is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Measuring the expression level of the selected biomarker (e.g. soluble CD95L) (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said one or two biomarkers proteins may be identified based on the known "separation profile" e. g., retention time, for that compound and measured using standard techniques.

Alternatively, the separated compounds may be detected and measured by, for example, a mass spectrometer.

Typically, levels of immunoreactive selected biomarker (e.g. soluble CD95L) in a sample may be measured by an immunometric assay on the basis of a double-antibody "sandwich" technique, with a monoclonal antibody specific for the selected biomarker (e.g. soluble CD95L). According to said embodiment, said means for measuring the expression level of the selected biomarker (e.g. soluble CD95L) are for example i) a buffer, ii) a monoclonal antibody that interacts specifically with the selected biomarker (e.g. soluble CD95L), iii) an enzyme-conjugated antibody specific for the selected biomarker (e.g. soluble CD95L) and a predetermined reference value of the selected biomarker.

As used herein a "ceramide" is any N-acylsphingosine. Ceramides include sphingolipids in which the sphingosine is acylated with a fatty acid acyl-CoA derivative to form an N-acylsphingosine. Ceramide may be either naturally occurring or chemically synthesized. Accordingly, the term "C16-ceramide" or "C16:0 ceramide" refers to N-palmitoyl-D-sphingosine.

As used herein the term "sphingomyelin" denotes any N-acylsphingosine conjugated to a phosphocholine group, the later forming the polar head group of the sphingomyelin (N-acylsphingosylphosphorylcholine). The acyl chain bound to the primary amino group of the sphingosine may be saturated or unsaturated, branched or unbranched. In one embodiment, the acyl chain comprises between 12 to 24 carbon atoms (C12-C24), at times between 14 to 20 carbon atoms. Accordingly, the term C16-sphingomyelin or "C16:0 sphingomyelin" refers to a sphingomyelin having an acyl chain of 16 carbons. The C16-sphingomyelin is typically a synthetic or semisynthetic or naturally occurring C16-sphingomyelin.

As used herein the term "glycosphingolipids" denotes any N-acylsphingosine conjugated to an oligosaccharide group, the later forming the polar head group of the glycosphingolipids. The acyl chain bound to the primary amino group of the sphingosine may be saturated or unsaturated, branched or unbranched. In one embodiment, the acyl chain comprises between 12 to 24 carbon atoms (C12-C24). Accordingly, the term C16-glycosphingolipids or "C16:0 glycosphingolipids" refers to a glycosphingolipid having an acyl chain of 16 carbons. The C16-glycosphingolipid is typically a synthetic or semisynthetic or naturally occurring C16-glycosphingolipid.

Typically, the C16-ceramide, or derivatives such as C-16-sphingomyelin or C16-glycosphingolipids according to the invention is administered in the form of a pharmaceutical composition. Thus, another aspect of the present invention provides pharmaceutical compositions comprising a therapeutically effective amount, of C16-ceramide, formulated together with one or more excipients, including additives and/or diluents. The phrase "pharmaceutically acceptable" is employed herein to refer to those compounds, materials, compositions, and/or dosage forms which are, within the scope of sound medical judgment, suitable for use in contact with the tissues of the subjects without excessive toxicity, irritation, allergic response, or other problem or complication, commensurate with a reasonable benefit/risk ratio. Typically, the pharmaceutical compositions may be specially formulated for administration in solid or liquid form, including those adapted for the following: (1) systemic or local oral administration, for example, drenches (aqueous or non-aqueous solutions or suspensions), tablets, boluses, powders, granules, pastes, or films; (2) parenteral administration, for example, by subcutaneous, intraperitoneal, intramuscular or intravenous injection as, for example, a sterile solution or suspension; (3) topical application, for example, as a cream, ointment or spray applied to the skin; or (4) intravaginally or intrarectally, for example, as a pessary, cream or foam.

In some embodiments, the C16-ceramide, C16-sphingomyelin or C16-glycosphingolipid is incorporated into liposomal vesicles. Examples of formulations of liposomes and other particulate carriers, particularly where ceramide is included are described in examples herein and in U.S. Patent Application Publication No. 2005/0025820. Further examples are described in Stover T et al., J Pharmacol Exp Ther., 2003, 307:468-475; and Stover T C, et al., Clin Cancer Res., 2005, 11:3465-3474. Liposomes used in methods according to the present invention typically have particle sizes in the range of about 1 nanometer to about 1 micron, inclusive, in diameter. Nano-sized liposomes having particle sizes in the range of about 1-100 nanometers, inclusive, in diameter are preferred. In embodiments in which a liposome nanocarrier is used, the liposome has a lipid-containing wall defining an internal volume. Further particulate carriers include other nanocarriers suitable for delivering the C16-ceramide, C16-sphingomyelin or C16-glycosphingolipid include but are not limited to nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further description of nanocarriers may be found in S. M. Moghimi et al., Nanomedicine: current status and future prospects, FASEB J. 2005, 19, 311-30.

The phrase "therapeutically-effective amount" as used herein means that amount of C-16 ceramide, C16-sphingomyelin or C16-glycosphingolipid that is effective for producing some desired therapeutic effect by blocking cancer cell motility. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A further aspect of the invention relates to a method for determining whether the EMT occurs in a tumor tissue sample obtained from a subject comprising determining the steps of i) determining the expression level of CerS6 or C-16 ceramide in the tumor tissue sample, ii) comparing the expression level determined at step i) with a predetermined reference value and iii) concluding that the EMT occurs in the tumor tissue sample when the expression level determined at step i) is lower than the predetermined reference value.

Determination of the level of C-16 ceramide in the tissue sample may be determined by any well known method in the art. Typically, the methods may comprise contacting the sample with a binding partner capable of selectively interacting with C-16 ceramide in the tumor tissue sample. In some aspects, the binding partners are antibodies, such as, for example, monoclonal antibodies or even aptamers. Alternatively, chromatographic methods (e.g. HPLC) or spectrometric methods (IFR, mass spectrometry) may also be used.

Determination of the expression level of CerS6 can be performed by a variety of techniques. Typically, the determination comprises contacting the sample with selective reagents such as probes, primers or ligands, and thereby detecting the presence, or measuring the amount of nucleic acids or proteins of interest (i.e. CerS6) originally in the sample.

In a particular embodiment, the expression level of CerS6 may be done by determining the quantity of mRNA in the tumor tissue sample obtained from the subject.

Methods for determining the quantity of mRNA are well known in the art. For example the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). In a particular embodiment, the expression level CerS6 is determined by RT-PCR, typically quantitative or semi-quantitative RT-PCR, even more typically real-time quantitative or semi-quantitative RT-PCR. Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more typically 85% identical and even more typically 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more typically of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they typically hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the expression level may be determined by determining the quantity of the CerS6 protein in the tissue sample. In a particular embodiment, the methods of the invention comprise contacting the tumor tissue sample with a binding partner capable of selectively interacting with the CerS6 protein present in the tumor tissue sample. The binding partner may be an antibody that may be polyclonal or monoclonal, typically monoclonal. In another embodiment, the binding partner may be an aptamer. In said embodiment, immunochemistry method well known in the art can be used for determining the expression level of CerS6.

In one embodiment of the present invention, the predetermined reference values are derived from the level of CerS6 or C16-ceramide of the invention in a control tissue sample wherein the EMT did not occur. Furthermore, retrospective measurement of the level of CerS6 or C16-ceramide in properly banked tumor tissue samples may be used in establishing these predetermined reference values.

In some embodiments, once it is concluded that the EMT occurs in the tumor tissue sample, the subject is administered with a therapeutically effective amount of a C-16-ceramide, a C-16-sphingomyelin or a C16-glycosphingolipid as above described for preventing or reducing the metastatic dissemination in the subject.

The invention will be further illustrated by the following figures and examples. However, these examples and figures should not be interpreted in any way as limiting the scope of the present invention.

FIGURES

FIG. 1. Treatment of mesenchymal breast cancer cells with a non-toxic amount of exogenous C16:0 ceramide reduces plasma membrane fluidity and prevents basal and CD95-mediated cell migration. A. The indicated cells were pre-incubated with or without a non-cytotoxic dose (1 μM) of C16:0 ceramide (C16-Cer) for 60 min, and were then incubated with or without cl-CD95L (100 ng/mL) for 30 min. Membrane fluidity was assessed by EPR. Values are means±SEM of four independent experiments (*, $p<0.05$; ns, not significant). B. Indicated cells were pretreated with or without C16:0 ceramide (1 M) for 60 min and were then incubated with or without cl-CD95L (100 ng/mL) for 24 h. Cell migration was assessed by the Boyden chamber assay. Bars=70 μm. Giemsa-stained cells that migrated to the lower side of the membrane were lysed and absorbance at 560 nm was recorded. Values represent the means and SEM of three independent experiments (*$p<0.05$).

EXAMPLE

Material & Methods

Cell Lines

The human cell lines derived from hematological cell lineage (Jurkat, CEM, H9, HL60, SKW6.4, K562, MOLT4, SR) were cultured in RPMI supplemented with 8% (v/v) heat-inactivated fetal calf serum (FCS) and 2 mM L-glutamine at 37° C. in a 5% CO2 incubator. All other cancer cell lines were cultured in DMEM supplemented with 8% (v/v) heat-inactivated FCS and 2 mM L-glutamine at 37° C. in a 5% CO2 incubator. The NCI-60 collection of human tumor cell lines came from Charles River Laboratories (Wilmington, Mass., USA). Other cells were purchased from American Type Culture Collection (LGC Standards, Molsheim, France). The human leukemic T-cell lines Jurkat and CEM, the lymphoma T-cell line H9, the promyelocytic cell line HL60, and the human B lymphoblastoid cell line SKW6.4 were cultured in RPMI supplemented with 8% (v/v) heat-inactivated fetal calf serum (FCS) and 2 mM L-glutamine at 37° C. in a 5% $CO_2$ incubator. The human breast cancer cell lines hs578T, MDA-MB-231, MDA-MB-468, T47D, ZR-75-1, and MCF7, as well as the human kidney carcinoma cell line Caki-1, the human colorectal carcinoma cell line HCT116, and the human glioma cell line U251 were cultured in DMEM supplemented with 8% (v/v) heat-inactivated FCS and 2 mM L-glutamine at 37° C. in a 5% $CO_2$ incubator. All cells were purchased from American Type Culture Collection (LGC Standards, Molsheim, France). The human mammary epithelial cell line MCF10A is spontaneously immortalized but not transformed. MCF10A cells infected with LXSN-K-RasV12 or an empty vector were kindly provided by Dr. B. H. Park (Baltimore, Md., USA)[16]. MCF10A cells were grown in DMEM/F12 medium supplemented with 5% horse serum, EGF (20 ng/mL), insulin (10 μg/mL), cholera toxin (100 ng/mL), and hydrocortisone (0.5 μg/mL) at 37° C. in a 5% $CO_2$ incubator. HMECs infected with a retrovirus carrying hTERT, Ras, and AgT were kindly provided by Dr R. A. Weinberg (Cambridge, Mass., USA)[4]. HMECs immortalized by hTERT and Ras were designated HMEC-TR.

In Vitro Motility Assay

Boyden chambers contained membranes with a pore size of 8 μm (Millipore, Molsheim, France). After hydration of the membranes, mesenchymal cells ($10^5$ cells per chamber) or epithelial cells ($3 \times 10^5$ cells per chamber) were added to the top chamber in low serum (1%)-containing medium. The bottom chamber was filled with low serum (1%)-containing medium in the presence or absence of cl-CD95L (100 ng/mL). Cells were cultured for 24 h at 37° C. To quantify migration, cells were mechanically removed from the top side of the membrane using a cotton-tipped swab, and migrating cells from the reverse side were fixed with methanol and stained with Giemsa. For each experiment, five representative pictures were taken for each insert, then cells were lyzed and absorbance at 560 nm correlated to the amount of Giemsa stain was measured.

EPR

Membrane fluidity was determined by a spin-labeling method using EPR, as previously described[27]. Briefly, plasma membranes of living cells were labeled by incubating cells for 15 min at 37° C. with 12-doxyl stearic acid (36 μg/mL), a fatty acid with a stable nitroxide radical ring at the C-12 position. Cells were then washed twice with PBS to remove excess 12-doxyl stearic acid and EPR spectra of the labeled samples were acquired at ambient temperature on a Bruker Elexsys EPR spectrometer operating at 3509.25 G center field, 20 mW microwave power, 9.86 GHz microwave frequency, 1.77 G modulation amplitude, and 100 kHz modulation frequency. Fluidity of the spin-labeled membranes was quantified by calculating the S parameter. An increase in the S parameter reflects a decrease in membrane fluidity, and vice versa.

Immunoblotting

Cells were lyzed for 30 min at 4° C. in lysis buffer (25 mM HEPES pH 7.4, 1% (v/v) Triton X-100, 150 mM NaCl, and 2 mM EGTA supplemented with a mixture of protease inhibitors). Protein concentration was determined by the bicinchoninic acid method (Pierce, Rockford, Ill., USA) according to the manufacturer's protocol. Proteins were resolved by 8, 10, or 12% SDS-PAGE and transferred to a nitrocellulose membrane (GE Healthcare, Buckinghamshire, UK). The membrane was blocked for 15 min with TBST (50 mM Tris, 160 mM NaCl, and 0.05% (v/v) Tween 20, pH 7.4) containing 5% (w/v) dried skimmed milk (TBSTM), and was then incubated overnight at 4° C. with the primary antibody diluted in TBSTM. The membrane was washed with TBST and was then incubated with peroxidase-labeled anti-mouse IgG1 or IgG2a (CliniSciences, Nanterre, France) for 45 min. Proteins were visualized using the enhanced chemiluminescence substrate kit (ECL Revel-BlOt®, Ozyme, Saint Quentin en Yvelines, France).

Results

EMT and Cl-CD95L-Induced Cell Migrations are Correlated with Increased Membrane Fluidity Using a transcriptomic analysis of 22 tumor cell lines of various histological origins [National Cancer Institute (NCI)] that respond differently to cytotoxic CD95L, we previously demonstrated that type I cells display a mesenchymal-like phenotype, whereas type II cells have an epithelial-like gene signature[1]. Cl-CD95L does not induce cell death but triggers cell motility[34]; therefore, we investigated whether EMT modifies the response of tumor cells to a CD95-driven pro-migratory cue. Using a Boyden chamber assay, cell motility was evaluated in various mesenchymal and epithelial-like breast cancer cells in the presence or absence of cl-CD95L. While mesenchymal-like cells migrated spontaneously across pore-containing membranes in the absence of cl-CD95L, epithelial cells did not. In addition, cl-CD95L treatment increased mesenchymal cell migration, but not epithelial cell migration. This suggests that CD95-mediated cell migration is blocked in the latter cells and/or promoted in the former cells.

Increased membrane fluidity can promote the invasion/motility of tumor cells[22, 30, 33, 39]; therefore, we next evaluated the membrane lipid packing densities of a large set of tumor cell lines. To this end, electron paramagnetic resonance (EPR) was used to quantify the S parameter, a biophysical parameter that is inversely correlated with membrane fluidity[2]. The S parameter was higher in epithelial tumor cells than in mesenchymal tumor cells (0.496±0.0088, n=17 versus 0.467±0.0215, n=20, p≤0.001), indicating that EMT led to membrane fluidization. Confirming this, the S parameter was higher in epithelial breast cancer cells than in mesenchymal breast cancer cells than in epithelial breast cancer cells (0.476±0.0069 n=6 versus 0.464±0.0043, n=6, p=0.0043). In addition, the membrane fluidity of mesenchymal-like MDA-MB-231 breast tumor cells increased following cl-CD95L treatment. To determine the role of plasma membrane fluidity in cell migration, MDA-MB-231 cells were pretreated with non-cytotoxic doses of the membrane stabilizing agent ursodeoxycholic acid (UDCA)[17] or the cyclopropyl fatty acid ester A2C, a compound that fluidifies plasma membranes[35]. Pre-incubation of MDA-MB-231 cells with UDCA slightly decreased basal membrane fluidity, although not significantly; however, this treatment abrogated the CD95-mediated increase in plasma membrane fluidity. By contrast, A2C treatment significantly enhanced both basal and CD95-induced cell membrane fluidity. Importantly, CD95-mediated migration of MDA-MB-231 cells was completely abolished by UDCA treatment but stimulated by A2C treatment. Collectively, these data indicate that plasma membrane fluidity increases during EMT and that this biophysical parameter has a pivotal function in both EMT-driven and CD95-mediated cell motility.

EMT Triggers Down-Regulation of CerS6.

Cholesterol and SLs participate in plasma membrane fluidity and compaction; therefore, we next investigated whether enzymes involved in the biosynthesis of these lipids are up- or down-regulated during EMT. To this end, a transcriptomic meta-analysis was performed using data from 22 tumor cell lines. These cell lines were epithelium-like or mesenchymal-like[25] and were previously categorized as type II and type I, respectively, based on their sensitivity to the CD95-mediated apoptotic signal[1]. Data were extracted from the NCBI Gene Expression Omnibus repository. The SAM tool (Significance Analysis of Microarrays) was used to identify 168 genes that were significantly up-regulated in type II cells and 542 genes that were significantly up-regulated in type I cells. Further analysis revealed that expression of CerS6, also known as LASS6, was significantly higher in epithelial-like (type II) cells than in mesenchymal-like (type I) cells. This in silico analysis was next validated experimentally at the mRNA. To rule out the possibility that this ceramide synthase was only associated with the way tumor cells respond to an apoptotic inducer, we next evaluated whether CerS6 was differentially expressed between NCI cell lines showing an epithelial or mesenchymal-like gene signature[26]. An in silico analysis performed on tumor cell lines classified as epithelial or mesenchymal-like cells according to their expression levels of E-cadherin (CDH1)(epithelial marker) and Vimentin (mesenchymal marker) confirmed that the level of CerS6 transcripts was reduced in mesenchymal-like cancer cells as compared to their counterparts exhibiting an epithelial-like gene signature. To confirm that CerS6 expression was down-regulated during EMT, we first evaluated the protein expression levels of two EMT markers, namely E-cadherin and Vimentin, in 47 NCI-60 tumor cell lines that have previously been reported to display an Epithelial or mesenchymal-like phenotype[24] We ranked these tumor cells based on their E-cadherin/Vimentin ratio into three groups: i) an epithelial group with high E-cadherin expression, ii) an undefined group that either expressed equally the two markers or did not express them, and iii) a mesenchymal group with high Vimentin expression. Minor differences were found when we compared our classification with the one from Peter's group[24]. Indeed, among the 47 tumor cell lines tested, only five of them (OSCAR-5, PC3, SW620, SR and IGROV-1) showed a difference of classification between the two studies. The protein expression levels of CerS6 were significantly increased in epithelial cells as compared to mesenchymal tumor cells. This suggests that CerS6 is a novel EMT-regulated gene, the expression of which in epithelial cells may alter the SL composition of plasma membranes.

To confirm that CerS6 expression was regulated during EMT, the level of CerS6 expression was evaluated in various well-established EMT models. Primary human mammary epithelial cells (HMECs) were used that have undergone sequential retroviral infections to express the telomerase catalytic subunit (hTERT), the large-T and small-t antigens of SV40, and the oncogenic allele of H-Ras (H-Ras$^{V12}$), and have thereby been converted to aggressive tumor cells[4, 8]. This stepwise EMT cellular model system, which gives rise to mammary cells exhibiting epithelial (E-cadherin) or mesenchymal-like (vimentin) gene signatures, confirmed that CerS6 expression was extinguished during EMT. To confirm this, CerS6 expression was evaluated in the immortal human mammary epithelial cell line MCF10A and its K-Ras$^{V12}$-expressing counterpart. Expression of the mesenchymal marker N-cadherin (CDH-2) was higher and expression of the epithelial marker E-cadherin was lower in MCF10A-K-Ras$^{V12}$ cells than in MCF10A cells, consistent with the former cells having undergone EMT[19]. Interestingly, EMT triggered by K-Ras$^{V12}$ expression was accompanied by a decrease in the protein level of CerS6. Stimulation with TGF-β can trigger MCF10A and HMEC-TR breast epithelial cells to undergo EMT[11]. This inducible EMT model was used to establish that CerS6 expression is consistently reduced during EMT.

Breast cancer is a heterogeneous pathology, with tumors being classified into various subtypes based on their genomic and clinical features[31]. While luminal A and B tumors express epithelial markers, such as E-cadherin, basal-like cancer cells have a mesenchymal-like phenotype and express markers such as vimentin and N-cadherin[26]. Importantly, prognosis is poorer in patients with basal breast tumors than in patients with luminal breast tumors, and EMT is associated with tumor aggressiveness and an increased risk of metastatic dissemination in these patients[26]. A meta-analysis of breast cancer patients using the bc-GenExMiner tool[13] showed that CerS6 expression was lower in basal tumors than in luminal tumors. Overall, these data strongly support that CerS6 expression is down-regulated in tumor cells undergoing EMT.

Overexpression of CerS6 in Mesenchymal Tumor Cells Decreases Membrane Fluidity and Inhibits Cell Motility.

To characterize the cellular function of CerS6 during EMT, CerS6 was overexpressed in two mesenchymal breast cancer cells, MDA-MB-231 and MDA-MB-468. Transduction of these cells with a CerS6-encoding retroviral vector generated stable cell populations overexpressing CerS6. Strikingly, CerS6 overexpression did not alter the expression levels of the mesenchymal marker vimentin or the epithelial marker E-cadherin, suggesting that EMT controlled CerS6 expression but not vice versa. Lipidomic analysis using gas chromatography and mass spectrometry showed that CerS6 overexpression significantly increased the C16-ceramide contents of both cell lines. However, this increase did not alter the total ceramide content, indicating that a compensatory process served to ensure that the total ceramide content did not change in CerS6-overexpressing cells. Modulation of CerS6 expression will affect the acyl-CoA pool, which is required for the biosynthesis of glycerophospholipids, including phosphatidylcho line, phosphatidylinosito 1, phosphatidylserine and phosphatidylethanolamine; therefore, the levels of these lipids were evaluated in MDA-MB-231 cells, MDA-MB-468 cells, and their CerS6-overexpressing counterparts. CerS6 overexpression did not significantly affect the glycerophospholipid content. Ceramide can be metabolized to sphingomyelin, the major plasma membrane SL; therefore, sphingomyelin content was also monitored. Whereas CerS6 overexpression did not affect the total amount of sphingomyelin, the level of C16-sphingomyelin was significantly higher in CerS6-overexpressing cells than in control cells. These findings show that CerS6 overexpression leads to the accumulation of C16:0 ceramide, which is metabolized to more complex SLs such as C16:0 sphingomyelin. CerS6 overexpression slightly, but significantly, reduced basal membrane fluidity and prevented cl-CD95L-induced membrane fluidization. In addition, CerS6 overexpression in these mesenchymal-like breast cancer cells reduced basal and inhibited CD95-mediated cell motility. These findings indicate that ectopic CerS6 expression in mesenchymal-like tumor cells increases levels of C16:0 ceramide and its derivative C16:0 sphingomyelin, which in turn reduces membrane fluidity and inhibits cell motility.

Down-Regulation of CerS6 in Epithelial Tumor Cells Enhances Membrane Fluidity and Stimulates Cell Migration.

To confirm that CerS6 reduces membrane fluidity and cell motility, a pharmacological inhibitor was used to perturb CerS6 activity in epithelial-like breast cancer cells, and the effects of this on plasma membrane fluidity and cell migration were determined. Fumonisin B$_1$ (FB1), a mycotoxin produced by *Fusarium moniliforme*, selectively inhibits CerS activity[36]. When the epithelial cell line MCF7 was treated with a non-cytotoxic concentration of FB1 for 48 hours, basal and CD95-induced membrane fluidity were slightly, but significantly, increased. In addition, FB1 treatment enhanced basal and CD95-mediated cell migration. To confirm these data, CerS6 expression was down-regulated in two epithelial breast cancer cells, MCF7 and T47D. These cells were transduced with lentiviruses encoding simultaneously GFP and shRNAs targeting different regions of CerS6 mRNA (shCerS6). All MCF7 cells and more than 80% of T47D cells were infected (GFP-positive). Consistent with the FACS analyses, CerS6 expression was efficiently silenced in MCF7 cells and to a lesser extent in T47D cells following transduction with lentiviruses containing either shCerS6. Furthermore, the reduction in CerS6 expression did not affect expression of EMT-related target genes, including E-cadherin and vimentin, confirming that CerS6 is not an EMT master regulator gene.

Lipidomic analysis showed that down-regulation of CerS6 expression in MCF7 and T47D cells did not alter their total ceramide contents, whereas the level of C16:0 ceramide was significantly reduced. By contrast, down-regulation of CerS6 expression was associated with a slight increase in the level of C18:0, C20:0, C24:0, or C24:1 ceramide, according to the cell line. CerS6 knockdown increased basal and CD95-mediated plasma membrane fluidity and cell migration in these epithelial cancer cells. Of note, the pro-migratory effect of cl-CD95L was less pronounced in shCerS6-treated MCF7 cells than in shCerS6-treated T47D cells. This may be because CerS6 expression was down-regulated more in MCF7 cells than in T47D cells, which led to a dramatic increase in the basal motility of MCF7 cells that might partially mask CD95-induced cell motility. Overall, these findings demonstrate that down-regulation of CerS6 expression in epithelial-like tumor cells enhances cell migration without affecting EMT.

C16-Ceramide, the Product of CerS6, Reduces Membrane Fluidity and Cell Migration.

Figure 1B:
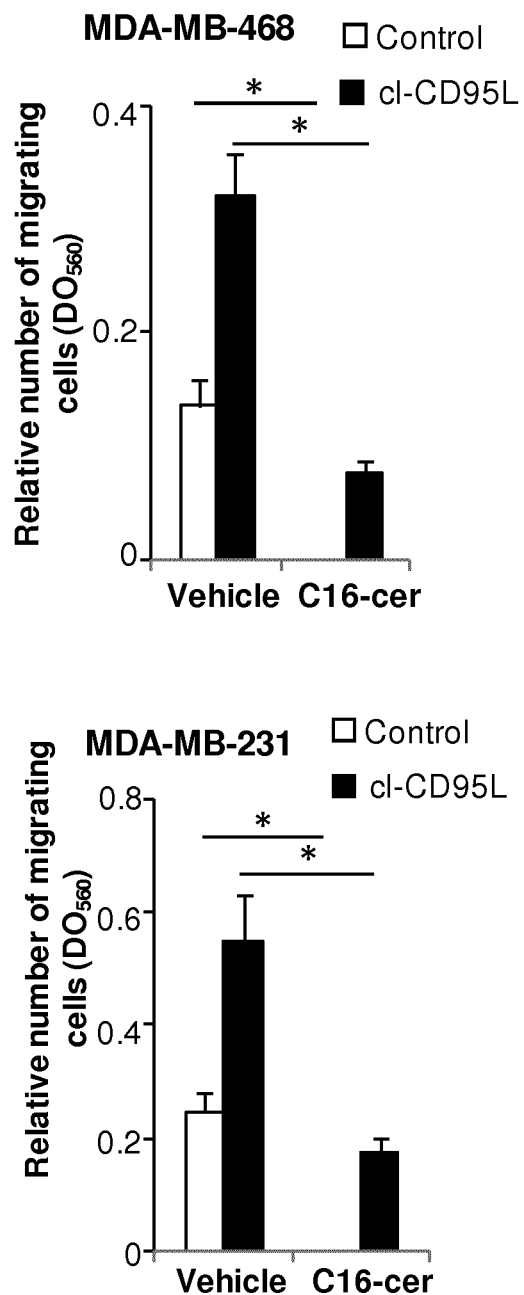

Finally, to show that CerS6 overexpression induced cell membrane compaction and thereby inhibited cell migration, we evaluated the impact of its main lipid product, C16-ceramide. To this end, two mesenchymal breast cancer cells were incubated for 24 hours with a non-cytotoxic concentration of C16:0 ceramide and membrane fluidity and cell motility were analyzed. While the addition of C16:0 ceramide slightly increased the basal S parameter in these cell lines (FIG. 1A), it completely inhibited the CD95-mediated increase in membrane fluidization (FIG. 1A). More importantly, basal and CD95-mediated migration of mesenchymal breast tumor cells was impaired when they were cultured in medium containing a non-cytotoxic concentration of C16-ceramide (FIG. 1B). These results indicate that exogenous C16-ceramide is adsorbed and retained in cell membranes, and confirm that an increased level of C16-ceramide, which is observed upon CerS6 overexpression, is instrumental in preventing CD95-mediated membrane fluidization and cell migration.

DISCUSSION

EMT is a crucial process in embryonic development that can be partly phenocopied in carcinogenesis, giving rise to aggressive tumors with increased metastatic capacity. In the present study, we demonstrate that CerS6 expression is down-regulated during EMT, leading to increased plasma membrane fluidity, which in turn promotes cell migration.

Cells undergoing EMT exhibit morphological changes and increased motility, which is linked to striking reductions in expression of epithelial markers, such as E-cadherin, and enhanced expression of mesenchymal markers, such as vimentin and N-cadherin. Using pharmacological and genetic approaches, we showed that the level of CerS6 expression does not affect EMT per se. This seems to disagree with data from the Hakomori group showing that pharmacological inhibition of glucosylceramide synthase or the addition of one of its products, gangliotetraosylceramide (Gg4), modulates cell motility and changes the expression ratio of EMT-related genes in various cellular models, including the epithelial breast cancer cell line MCF-7[6]. One explanation for this discrepancy is that the carbohydrate moiety complexity of Gg4 allows it to target other unidentified molecular targets and thereby exert additional effects on EMT compared to C16-ceramide and C16-sphingomyelin. In support of this hypothesis, the ganglioside GM2, whose expression is also decreased by inhibition of glucosylceramide synthase activity, does not reverse TGF-β-induced EMT of NMuMG cells, whereas Gg4 does[6]. In addition to the carbohydrate moiety, our findings provide insight into the pivotal roles played by the C16:0 fatty acid chain of ceramide and its derivatives in biological functions such as cell motility.

Okazaki and colleagues recently showed that sphingomyelin impairs CXCL12-mediated cell migration[3]. The current study shows that CerS6 overexpression is associated with an increase in the C16:0 sphingomyelin content; therefore, we cannot exclude the possibility that sphingomyelin contributes to the phenotypes observed. However, given that CD95-mediated membrane fluidization and cell migration are inhibited by pre-incubation with exogenous C16-ceramide for a short period (60 minutes), C16-ceramide itself likely contributes to the modulation of membrane fluidity and cell motility during EMT.

Glycosphingolipids (GSLs) modulate various cell signaling pathways by regulating the activities of tyrosine kinase receptors[9, 21], and more specifically, epidermal growth factor (EGF) receptor[9]. Based on our recent findings showing that cl-CD95L induces a phosphoinositide 3-kinase (PI3K)-driven pro-migratory signaling pathway in mesenchymal breast tumor cells via recruitment of EGF receptor[18], we investigated whether C16-ceramide can prevent this signaling pathway. Analysis of phosphorylation at serine 473 of Akt, a hallmark of PI3K activation, demonstrated that C16-ceramide did not affect the CD95-mediated PI3K signaling pathway. This indicates that C16-ceramide does not interfere with the initial steps of pro-migratory CD95-mediated cell signaling. The mechanistic link between CD95L and plasma membrane fluidization remains uncertain and requires further investigation.

Exogenous short-chain ceramides such as C2-ceramide inhibit migration of lung cancer cells in response to nicotine via activation of protein phosphatase 2A[38]. This previous study suggested that C2-ceramide directly affects cell migration. However, the authors did not eliminate the possibility that C2-ceramide that accumulates in the lipid bilayers of pulmonary cells is hydrolyzed by acid ceramidase to form sphingosine that enters the salvage pathway to form new ceramides through the activities of CerS such as CerS6. In this regard, it would be interesting to investigate the activity of CerS6 in pulmonary epithelial cells exposed to nicotine.

CerS6 expression was modulated in various cancer cell lines with epithelial- or mesenchymal-like gene signatures, in well-defined inducible EMT models, and also in a large panel of women affected by luminal or basal breast cancers, which show an epithelial- and mesenchymal-like gene signature, respectively[26]. Accordingly, we predict that in women with aggressive basal breast cancers in which CerS6 is not expressed, a slight increase in the level of C16- ceramide and its derivatives may help to reduce their elevated risk of metastatic dissemination.

REFERENCES

Throughout this application, various references describe the state of the art to which this invention pertains. The disclosures of these references are hereby incorporated by reference into the present disclosure.
1. Algeciras-Schimnich A, Pietras E M, Barnhart B C, Legembre P, Vijayan S, Holbeck S L et al. Two CD95 tumor classes with different sensitivities to antitumor drugs. Proc Natl Acad Sci USA 2003; 100: 11445-11450.
2. Alonso A, Meirelles N C, Tabak M. Effect of hydration upon the fluidity of intercellular membranes of stratum corneum: an EPR study. Biochim Biophys Acta 1995; 1237: 6-15.
3. Asano S, Kitatani K, Taniguchi M, Hashimoto M, Zama K, Mitsutake S et al. Regulation of cell migration by sphingomyelin synthases: sphingomyelin in lipid rafts decreases responsiveness to signaling by the CXCL12/CXCR4 pathway. Mol Cell Biol 2012; 32: 3242-3252.
4. Elenbaas B, Spirio L, Koerner F, Fleming M D, Zimonjic D B, Donaher J L et al. Human breast cancer cells generated by oncogenic transformation of primary mammary epithelial cells. Genes Dev 2001; 15: 50-65.
5. Goni F M, Alonso A. Effects of ceramide and other simple sphingolipids on membrane lateral structure. Biochim Biophys Acta 2009; 1788: 169-177.
6. Guan F, Handa K, Hakomori S I. Specific glycosphingolipids mediate epithelial-to-mesenchymal transition of human and mouse epithelial cell lines. Proc Natl Acad Sci USA 2009; 106: 7461-7466.
7. Gulbins E, Dreschers S, Wilker B, Grassme H. Ceramide, membrane rafts and infections. J Mol Med (Berl) 2004; 82: 357-363.
8. Hahn W C, Dessain S K, Brooks M W, King J E, Elenbaas B, Sabatini D M et al. Enumeration of the simian virus 40 early region elements necessary for human cell transformation. Mol Cell Biol 2002; 22: 2111-2123.
9. Hanai N, Dohi T, Nores G A, Hakomori S. A novel ganglioside, de-N-acetyl-GM3 (II3NeuNH2LacCer), acting as a strong promoter for epidermal growth factor receptor kinase and as a stimulator for cell growth. J Biol Chem 1988; 263: 6296-6301.
10. Hannun Y A, Obeid L M. Principles of bioactive lipid signalling: lessons from sphingolipids. Nat Rev Mol Cell Biol 2008; 9: 139-150.
11. Hesling C, Fattet L, Teyre G, Jury D, Gonzalo P, Lopez J et al. Antagonistic regulation of EMT by TIF1gamma and Smad4 in mammary epithelial cells. EMBO Reports 2011; 12: 665-672.
12. Hoogwater F J, Nijkamp M W, Smakman N, Steller E J, Emmink B L, Westendorp B F et al. Oncogenic K-Ras turns death receptors into metastasis-promoting receptors in human and mouse colorectal cancer cells. Gastroenterology 2010; 138: 2357-2367.
13. Jezequel P, Frenel J S, Campion L, Guerin-Charbonnel C, Gouraud W, Ricolleau G et al. bc-GenExMiner 3.0: new mining module computes breast cancer gene expression correlation analyses. Database: the journal of biological databases and curation 2013; 2013: bas060.
14. Kischkel F C, Hellbardt S, Behrmann I, Germer M, Pawlita M, Krammer P H et al. Cytotoxicity-dependent APO-1 (Fas/CD95)-associated proteins form a death-inducing signaling complex (DISC) with the receptor. Embo J 1995; 14: 5579-5588.
15. Kleber S, Sancho-Martinez I, Wiestler B, Beisel A, Gieffers C, Hill O et al. Yes and PI3K bind CD95 to signal invasion of glioblastoma. Cancer Cell 2008; 13: 235-248.
16. Konishi H, Karakas B, Abukhdeir A M, Lauring J, Gustin J P, Garay J P et al. Knock-in of mutant K-ras in nontumorigenic human epithelial cells as a new model for studying K-ras mediated transformation. Cancer Res 2007; 67: 8460-8467.
17. Luciano L, Konitz H, Reale E. Localization of cholesterol in the colonic epithelium of the guinea pig: regional differences and functional implications. Cell and tissue research 1989; 258: 339-347.
18. Malleter M, Tauzin S, Bessede A, Castellano R, Goubard A, Godey F et al. CD95L cell surface cleavage triggers a prometastatic signaling pathway in triple-negative breast cancer. Cancer Res 2013; 73: 6711-6721.
19. Morel A P, Lievre M, Thomas C, Hinkal G, Ansieau S, Puisieux A. Generation of breast cancer stem cells through epithelial-mesenchymal transition. PLoS One 2008; 3: e2888.
20. Mullen T D, Hannun Y A, Obeid L M. Ceramide synthases at the centre of sphingolipid metabolism and biology. Biochem J 2012; 441: 789-802.
21. Mutoh T, Tokuda A, Miyadai T, Hamaguchi M, Fujiki N. Ganglioside GM1 binds to the Trk protein and regulates receptor function. Proc Natl Acad Sci USA 1995; 92: 5087-5091.
22. Nakazawa I, Iwaizumi M. A role of the cancer cell membrane fluidity in the cancer metastases: an ESR study. Tohoku J Exp Med 1989; 157: 193-198.
23. O'Reilly L A, Tai L, Lee L, Kruse E A, Grabow S, Fairlie W D et al. Membrane-bound Fas ligand only is essential for Fas-induced apoptosis. Nature 2009; 461: 659-663.
24. Pewzner-Jung Y, Park H, Laviad E L, Silva L C, Lahiri S, Stiban J et al. A critical role for ceramide synthase 2 in liver homeostasis: I. alterations in lipid metabolic pathways. J Biol Chem 2010; 285: 10902-10910.
25. Ross D T, Scherf U, Eisen M B, Perou C M, Rees C, Spellman P et al. Systematic variation in gene expression patterns in human cancer cell lines. Nat Genet 2000; 24: 227-235.
26. Sarrio D, Rodriguez-Pinilla S M, Hardisson D, Cano A, Moreno-Bueno G, Palacios J. Epithelial-mesenchymal transition in breast cancer relates to the basal-like phenotype. Cancer research 2008; 68: 989-997.
27. Sergent O, Tomasi A, Ceccarelli D, Masini A, Nohl H, Cillard P et al. Combination of iron overload plus ethanol and ischemia alone give rise to the same endogenous free iron pool. Biometals: an international journal on the role of metal ions in biology, biochemistry, and medicine 2005; 18: 567-575.
28. Silva L C, de Almeida R F, Castro B M, Fedorov A, Prieto M. Ceramide-domain formation and collapse in lipid rafts: membrane reorganization by an apoptotic lipid. Biophys J 2007; 92: 502-516.
29. Silva L C, Ben David O, Pewzner-Jung Y, Laviad E L, Stiban J, Bandyopadhyay S et al. Ablation of ceramide synthase 2 strongly affects biophysical properties of membranes. Journal of lipid research 2012; 53: 430-436.
30. Sok M, Sentjurc M, Schara M, Stare J, Rott T. Cell membrane fluidity and prognosis of lung cancer. The Annals of thoracic surgery 2002; 73: 1567-1571.
31. Sorlie T, Perou C M, Tibshirani R, Aas T, Geisler S, Johnsen H et al. Gene expression patterns of breast carcinomas distinguish tumor subclasses with clinical implications. Proc Natl Acad Sci USA 2001; 98: 10869-10874.

32. Strasser A, Jost P J, Nagata S. The many roles of FAS receptor signaling in the immune system. Immunity 2009; 30: 180-192.

33. Taraboletti G, Perin L, Bottazzi B, Mantovani A, Giavazzi R, Salmona M. Membrane fluidity affects tumor-cell motility, invasion and lung-colonizing potential. Int J Cancer 1989; 44: 707-713.

34. Tauzin S, Chaigne-Delalande B, Selva E, Khadra N, Daburon S, Contin-Bordes C et al. The naturally processed CD95L elicits a c-yes/calcium/PI3K-driven cell migration pathway. PLoS Biol 2011; 9: e1001090.

35. Vlasic N, Medow M S, Schwarz S M, Pritchard K A, Jr., Stemerman M B. Lipid fluidity modulates platelet aggregation and agglutination in vitro. Life sciences 1993; 53: 1053-1060.

36. Wang E, Norred W P, Bacon C W, Riley R T, Merrill A H, Jr. Inhibition of sphingolipid biosynthesis by fumonisins. Implications for diseases associated with *Fusarium moniliforme*. J Biol Chem 1991; 266: 14486-14490.

37. Weinmann A, Galle P R, Teufel A. LASS6, an additional member of the longevity assurance gene family. Int J Mol Med 2005; 16: 905-910.

38. Xu L, Deng X. Suppression of cancer cell migration and invasion by protein phosphatase 2A through dephosphorylation of mu- and m-calpains. J Biol Chem 2006; 281: 35567-35575.

39. Zeisig R, Koklic T, Wiesner B, Fichtner I, Sentjurc M. Increase in fluidity in the membrane of MT3 breast cancer cells correlates with enhanced cell adhesion in vitro and increased lung metastasis in NOD/SCID mice. Arch Biochem Biophys 2007; 459: 98-106.

The invention claimed is:

1. A method for inhibiting or reducing metastatic dissemination in a subject suffering from a cancer comprising the steps of:
   i) measuring an expression level of at least one biomarker selected from the group consisting of: soluble CD95L and epithelial-to-mesenchymal transition (EMT) promoting factors in a sample obtained from the subject,
   ii) comparing the expression level measured at step i) with a reference expression level of the biomarker determined in an individual who has the same cancer but for whom metastatic dissemination did not occur, and
   iii) administering to the subject a therapeutically effective amount of at least one compound selected from the group consisting of C16-ceramide, C16-sphingomyelin and C16-glycosphingolipid when the expression level determined at step i) is higher than the reference biomarker expression level.

2. The method of claim 1 wherein the subject suffers from a cancer selected from the group consisting of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers.

3. The method of claim 1 wherein the subject suffers from a triple negative breast cancer.

4. The method of claim 1 wherein the EMT-promoting factor is TGFbeta.

5. The method of claim 1 wherein the C16-ceramide, C16-sphingomyelin or C16-glycosphingolipid is incorporated into liposomal vesicles.

\* \* \* \* \*